United States Patent
Kim

(10) Patent No.: US 9,179,841 B2
(45) Date of Patent: Nov. 10, 2015

(54) ADAPTIVE OPTICS OPHTHALMIC IMAGER WITHOUT WAVEFRONT SENSOR OR WAVEFRONT CORRECTOR

(71) Applicant: Myung K. Kim, Tampa, FL (US)

(72) Inventor: Myung K. Kim, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 190 days.

(21) Appl. No.: 13/901,972

(22) Filed: May 24, 2013

(65) Prior Publication Data

US 2013/0250240 A1 Sep. 26, 2013

Related U.S. Application Data

(63) Continuation of application No. PCT/US2011/061798, filed on Nov. 22, 2011.

(60) Provisional application No. 61/416,836, filed on Nov. 24, 2010.

(51) Int. Cl.
 *A61B 3/14* (2006.01)

(52) U.S. Cl.
 CPC .................................. *A61B 3/14* (2013.01)

(58) Field of Classification Search
 CPC ...... A61B 3/10–3/14; A61B 3/00; H01S 3/10
 USPC .................. 351/206, 221, 246; 359/3, 11; 250/201.9
 See application file for complete search history.

(56) References Cited

U.S. PATENT DOCUMENTS

| | | | |
|---|---|---|---|
| 4,650,302 A | 3/1987 | Grant | |
| 6,488,377 B2 | 12/2002 | Matsumoto | |
| 6,547,395 B1 | 4/2003 | Neal et al. | |
| 6,758,564 B2 | 7/2004 | Ferguson | |
| 6,952,435 B2 | 10/2005 | Lai et al. | |
| 7,289,253 B2* | 10/2007 | Thomas | 359/11 |
| 2006/0087617 A1* | 4/2006 | Roorda | 351/221 |
| 2007/0253057 A1 | 11/2007 | Potsaid et al. | |
| 2008/0265130 A1* | 10/2008 | Colomb et al. | 250/201.9 |

OTHER PUBLICATIONS

E. Cuche et al., Digital holography for quantitative phase-contrast imaging. Optics Letters. 1999. vol. 24 (No. 5):291-293.

(Continued)

*Primary Examiner* — Ricky Mack
*Assistant Examiner* — Mustak Choudhury
(74) *Attorney, Agent, or Firm* — Smith & Hopen, P.A.; Molly L. Sauter; Michele L. Lawson

(57) ABSTRACT

The invention utilizes a digital holographic adaptive optics (DHAO) system to replace hardware components in a conventional AO system with numerical processing for wavefront measurement and compensation of aberration by the principles of digital holography. Wavefront sensing and correction by DHAO have almost the full resolution of a CCD camera. The approach is inherently faster than conventional AO because it does not involve feedback and iteration, and the dynamic range of deformation measurement is essentially unlimited. The new aberration correction system can be incorporated into a conventional fundus camera with minor modification and achieve high resolution imaging of a retinal cone mosaic. It can generate profiles of the retinal vasculature and measure blood flow. It can also provide real-time profiles of ocular aberration during refractive (Lasik) surgery and generate three-dimensional maps of intraocular debris.

23 Claims, 5 Drawing Sheets

(56) References Cited

OTHER PUBLICATIONS

C. Mann et al., High-resolution quantitative phase-contrast microscopy by digital holography. Optics Express. 2005. vol. 13 (No. 22):8693-8698.

M. K. Kim, Principles and techniques of digital holographic microscopy. SPIE Reviews. 2010. vol. 1:1-50.

International Search Report for PCT/US2011/061798 (filing date of Nov. 22, 2011) with a mailing date of Jun. 29, 2012, Applicant: University of South Florida et al.

Preliminary Report of Patentability for PCT/US2011/061798 (filing date of Nov. 22, 2011) with an issuance date of May 28, 2013, Applicant: University of South Florida et al.

* cited by examiner

ADAPTIVE OPTICS OPHTHALMIC IMAGER WITHOUT WAVEFRONT SENSOR OR WAVEFRONT CORRECTOR

CROSS-REFERENCE TO RELATED APPLICATIONS

This application is a continuation of prior filed International Application Serial Number PCT/US2011/061798 filed Nov. 22, 2011, which claims priority from U.S. Provisional Application No. 61/416,836 filed on Nov. 24, 2010, entitled "Adaptive Optics Ophthalmic Imager Without Wavefront Sensor Or Wavefront Corrector".

GOVERNMENT SUPPORT

This invention was made with government support under Grant No. 0755705 awarded by the National Science Foundation. The government has certain rights in the invention.

FIELD OF THE INVENTION

This invention relates to ophthalmic imaging. More specifically, it relates to adaptive optics ophthalmic imager having numerical processing for wavefront measurement and compensation.

BACKGROUND OF THE INVENTION

Imaging of the eye is important both in order to understand the process of vision and to correct or repair any defects in the vision system. Imaging of the eye is also inherently difficult in several respects. For example, relatively small aperture of the pupil and low reflectivity of the retina limits the amount of light available for imaging with an external instrument to about $10^{-5} \sim 10^{-3}$ of the input, depending on the wavelength. Highly directional lasers and high sensitivity detectors are used in modern instruments such as scanning laser ophthalmoscope (SLO) or optical coherence tomography (OCT). These conventional fundus cameras provide a macroscopic view of the living retina, but they do not have the transverse resolution needed to reveal retinal features on the spatial scale of single cells (~2 μm). With typical values of the pupil aperture 3 mm, retinal distance 22 mm, and index of refraction 1.33, the numerical aperture of the eye is less than 0.1, which corresponds to diffraction limited resolution of 3.3 μm at the wavelength 0.6 μm. The pupil can be dilated to 5 mm or more but then imperfections, i.e. aberrations, of the cornea and lens prevent diffraction-limited imaging.

Adaptive optics (AO), originally developed for astronomical telescopes, reduces the effect of atmospheric turbulence by measuring the distortion of the wavefront arriving from a point source (guide star) and using the information to compensate for the distortions in the objects to be imaged. When applied to ocular imaging, the "guide star" is provided by a narrow laser beam focused on a spot of the retina. Most commonly a Shack-Hartmann wavefront sensor is used to measure the wavefront of the reflected light. The wavefront distortion is then compensated for using a wavefront corrector, such as deformable mirror or liquid crystal spatial light modulator. The sensor and corrector typically has a few hundred elements, allowing for adjustment of similar number of coefficients in the Zernike aberration polynomials. Several iterations of sensing, computation, and corrections are carried out in a feedback loop to reach a stable state. AO is incorporated in SLO, OCT, and laser refractive surgery. By AO compensation of the aberration, individual photoreceptor cells are resolved in the cone mosaic of the fovea.

Therefore, ophthalmic imaging is limited by the small aperture of the pupil and the aberration of the eye, it is difficult to resolve individual photoreceptor cells of retina. Current technology of adaptive optics solves this problem by employing a wavefront sensor to measure the aberration and a wavefront corrector to compensate for the aberration. But they limit the resolution and speed of the adaptive imaging system and also drive up its cost.

SUMMARY OF INVENTION

The present invention provides a method of adaptive optics ophthalmic imaging. The method dispenses with wavefront sensor and corrector, and replaces these hardware components with numerical processing for wavefront measurement and compensation. It substantially reduces complexity and cost of the optomechanical system. Wavefront sensing and correction has almost full resolution of the CCD camera. It does not involve electronic-numerical-mechanical feedback, which can improve the imaging speed and the dynamic range. The new aberration correction system can be incorporated into a conventional fundus camera with minor modification and achieve high resolution imaging of retinal cone mosaic. It can generate profiles of retinal vasculature and measurement of blood flow. It can provide real time profiles of ocular aberration during refractive surgery (Lasik) and generate three-dimensional map of intraocular debris.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
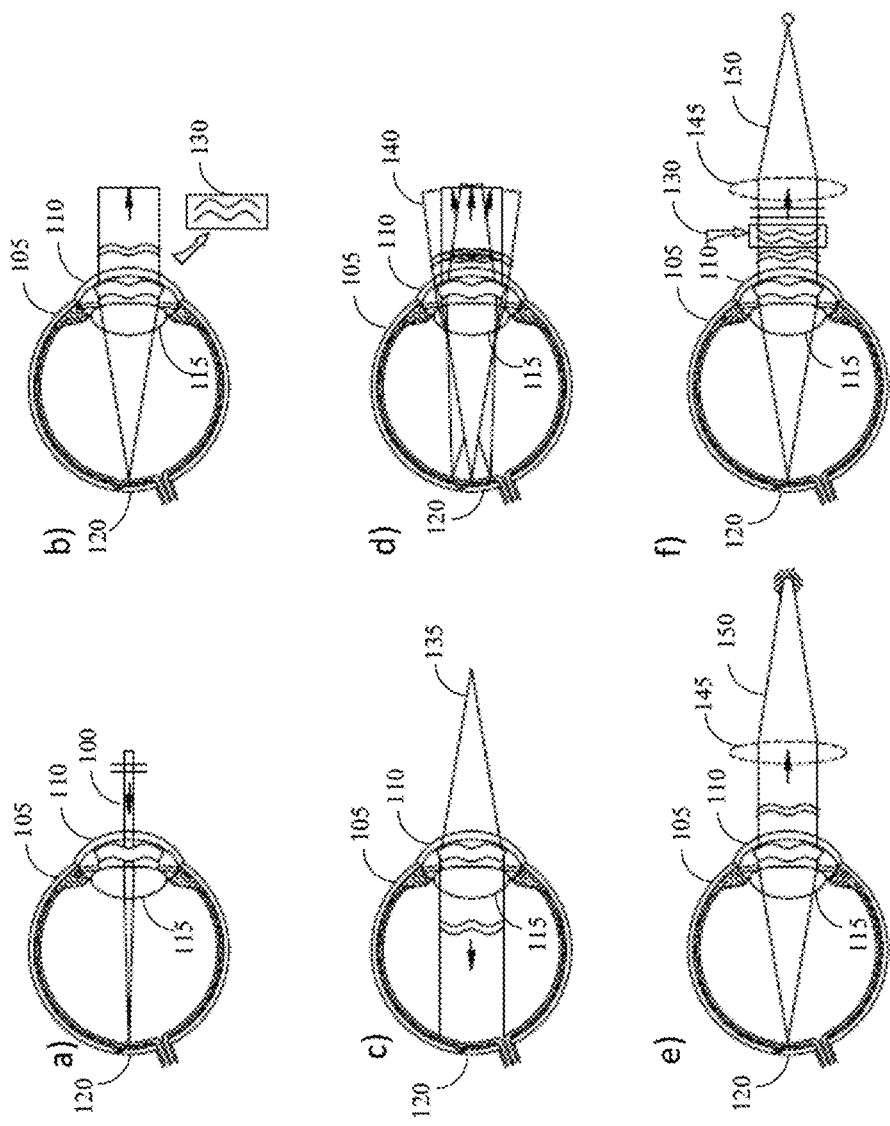
FIG. 1 is an illustration of digital holographic adaptive optics (DHAO) principle.

The invention is a new AO system that dispenses with wavefront sensor and corrector. Wavefront sensor and corrector are well developed essential components of current AO technology. They are also the parts that require high degree of delicate alignment and maintenance, constrain the resolution, dynamic range, and speed, as well as driving up the cost. The invention replaces these hardware components with numerical processing for wavefront measurement and compensation of aberration through principles of digital holography. The system can be designed around a conventional fundus camera. For example, with a modification that allows introduction of a reference illumination. As described below, digital holography is ideally suited for accurate and efficient determination of the wavefront profile as well as direct numerical manipulation of the wavefront profile. The wavefront sensing is achieved by analyzing the interference between the reflection of the "guide star" spot and a reference illumination. The interference pattern, the hologram, contains the complete information of the wavefront distortion due to aberrations, which can be extracted by straightforward numerical processing. For imaging, the retina is flood illuminated and another hologram is acquired, which is again numerically processed to reconstruct the image. In digital holography, the image is represented as an array of complex numbers, including both the amplitude and phase of the optical field. The wavefront, i.e. phase, distortion measured in the first step can then be subtracted from the holographic image of the second exposure, thus removing the effect of aberration.

The DHAO substantially reduces complexity, and therefore the cost, of the optomechanical system. Wavefront sensing and correction has almost full resolution of the CCD camera. It does not involve electronic-numerical-mechanical feedback. Numerical computation of holographic images is comparable or faster than the conventional AO feedback loop. Dynamic range of deformation measurement is essentially unlimited—large deformations only result in the wrapping of the phase profile. If necessary, phase unwrapping can be done using available software algorithms. Digital holography also offers optical phase unwrapping technique that avoids some of the problems with software unwrapping.

Incorporation of digital holography (DH) in an ophthalmic imaging system can offer a number of additional novel imaging capabilities. Often the field of view (FOV) for retinal imaging is limited by the curvature of the retinal surface. DH image has full 3D content of the optical field, which can be used to extract in-focus image of a larger area of the retina despite the curvature. DH is highly effective in imaging particulate objects such as intraocular debris and determining their 3D locations with high precision, producing 3D distribution map of such particles from a single hologram. Low coherence holographic methods, or other techniques, are available to focus on separate components of the eye such as the crystalline lens or cornea while optical signals from other parts are suppressed. By offering many novel imaging techniques that are difficult or infeasible in real space optics, digital holography has a real potential to change the paradigm in many areas of imaging science including ophthalmology, microscopy, metrology, and other areas of biomedical imaging.

The basic principle of DHAO is described using FIG. 1. It is a two exposure process. First, in FIG. 1(a), a narrow collimated laser beam 100 enters the eye 105 through the cornea 110 and the lens 115 of the eye 105, which forms a focused spot on the retina 120, the so-called "guide star." The diffraction-limited spot size is typically a few micrometers. The light scatters and reflects from the guide star spot and exits the eye 105 with a broad coverage 125 of the cornea 110 and the lens 115, FIG. 1(b). Ideally, the emergent beam 125 would be collimated and its wavefront 130 planar, whereas any aberration of the eye's 105 optics causes distortion of the wavefront 130. The phase profile of the wavefront 130 is captured by digital holography and numerically stored. In the second step, for full-field imaging of the retina 120, a focused source 135 at the front focus of the eye lens 115 results in a collimated illumination of the retina 120, FIG. 1(c). The illumination does contain phase distortion due to the eye's 105 aberration, but this does not affect the final intensity image of the eye 105. The complex, i.e., amplitude and phase, optical field 140 exiting the eye 105 is again captured by digital holography at a plane in front of the cornea 110, FIG. 1(d). The captured complex optical field 140 contains all the information necessary to reconstruct the image of the retina 120 by using a numerical lens 145 and numerically propagating an appropriate distance 150, FIG. 1(e). But the phase distortion degrades the point spread function of the resultant image, which can be compensated for by numerically subtracting the stored phase profile 130 from the first step, FIG. 1(f). This description of DHAO assumes: (i) that the guide star input beam is narrow enough that the aberration across it is negligible, but large enough that the guide star spot is as small as possible compared to the retinal cell; and (ii) that most of the aberration is in the anterior region of the eye, i.e., the lens and the cornea, so that the aberration experienced by the light from various parts of the retina is approximately equal, see FIG. 1(d). Similar assumptions are necessary in conventional AO and they are not any more severe in DHAO.

Figure 2:
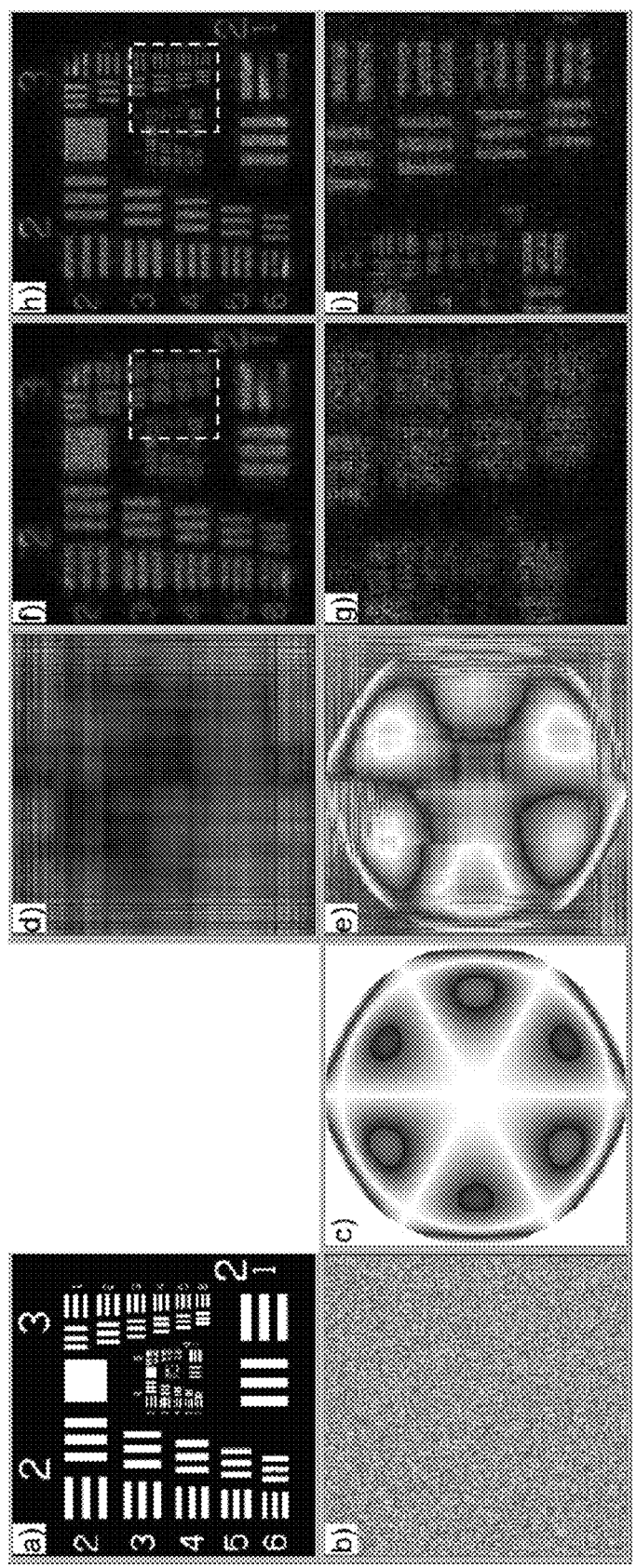
FIG. 2. is a depiction of simulation of DHAO process. (a) Assumed amplitude pattern on retina; b) phase noise of retinal surface; (c) assumed aberration of the eye; (d) amplitude of exit field; (e) phase of exit field, representing measured aberration of the eye; (f) uncorrected image of retina and (g) its detail; and (h) corrected image of retina and (i) its detail.

The process of DHAO is illustrated using the simulation images in FIG. 2, Amplitude images are shown in gray scale and phase images (b), (c), and (e) in blue-white-red color scale, representing the range of phase from $-\pi$ to $+\pi$. The retinal surface is represented with a resolution target pattern, FIG. 2(a). The field is assumed to be 2500 µm×2500 µm with 512 pixels×512 pixels. The simulated pattern is not meant to be a correctly scaled copy of the United States Air Force (USAF) resolution target. The retinal surface irregularity is represented with a random phase distribution of the retinal surface, FIG. 2(b). The eye is modeled to consist of a lens of focal length 25 mm and the retinal surface located at the focal plane of the lens. The lens is also assumed to contain an aberration in the form of a phase distortion corresponding to one of the Zernike polynomials $aZ_5^3(\rho, \phi)=a(5\rho^5-4\rho^3)\cos 3\phi$, defined on a circle of diameter 2500 µM and amplitude $a=4\pi$, as depicted in FIG. 2(c). In sensing, the amplitude and phase profiles of the optical field emerging from a small area of the retina, i.e., the guide star, are shown in FIGS. 1(d) and 1(e). It is an approximate plane wave, with phase distortion due to the assumed aberration of the lens and the phase noise of the retina. For imaging, the light enters the eye lens, with aberration, and illuminates the retina, from which it reflects and exits the lens, again with the aberration. The emerging optical field is diffuse with random phase distribution, which can be captured in the experiment as a hologram. To reconstruct the image of the retina, one can simulate the propagation of light through an imaging lens (e.g., f=25 mm) and an appropriate distance (z=25 mm) to the image plane. The resultant image is shown in FIG. 2(f) and a magnified view of the dotted square area is shown in FIG. 2(g). In order to compensate for the aberration, the aberration field represented in FIGS. 2(d) and 2(e) is conjugated and multiplied to the hologram before propagating through the imaging lens to the image plane. The result is shown in FIG. 2(h), and a magnified view of the dotted square area is shown in FIG. 2(i). Comparison of FIGS. 2(f) and 2(h), or 2(g) and 2(i), clearly displays DHAO in resolution improvement.

Figure 3:
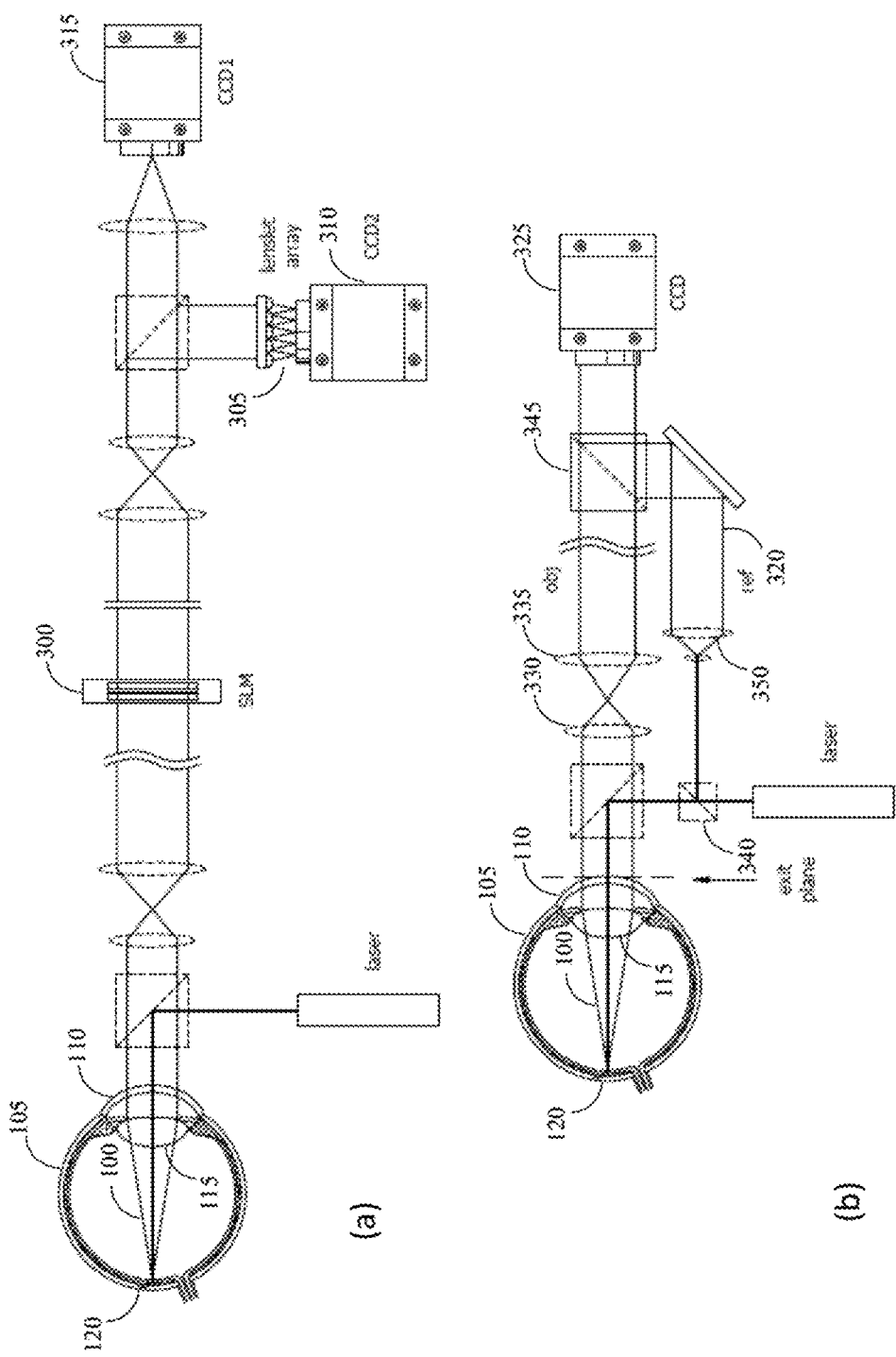
FIG. 3. is an illustration of (a) conventional AO apparatus. (b) DHAO apparatus. The CCD camera plane is conjugate to the hologram plane H. R, retinal plane; C, corneal lens; A, aberrator.

Conventional AO (cAO) is shown in FIG. 3(a). In cAO, reflection from the "guide star" spot illuminates the wavefront sensor. Deflection of focal spots of the lenslets 305 are sensed by the camera CCD2 310. The information is used in a computer algorithm to calculate appropriate deformation of the waveform corrector, here represented with a transmission spatial light modulator (SLM) 300. The eye is then flood illuminated (not shown) and imaged by the camera CCD1 315, with the aberration having been compensated for by the SLM 300.

DHAO system does not have the SLM 300, lenslet array 305, or the second CCD 310. Instead it has a collimated beam of light 320 to provide the reference for holographic interference. The principle of DHAO is experimentally demonstrated using the apparatus shown in FIG. 3(b). First, a narrow collimated HeNe laser beam 100 enters the eye 105 and is focused on the retinal surface 120. For this proof-of-principle experiment, the eye is modeled by a combination of a simple lens (f=25 mm) (C) and a printed-on-paper resolution target (R) placed at the focal plane of the lens. The spot size on the retina is estimated to be ~50 μm. The aberration of the eye 105 is imitated by placing an irregular piece of glass (A) in front of the lens. The complex optical field of the emergent light is captured by the CCD camera 325, which is focused at the plane (H) through the relay lenses L2 330 and L3 335. The reference 320 for the holographic imaging is provided by the beam splitter (BS1) 340, the beam expander 350, and the beam combiner (BC) 345. The reference 320 is slightly tilted for off-axis holography configuration. For the full-field imaging of the retinal surface, another lens L1 is inserted so that its focus coincides with that of the eye lens, C. A second exposure of the hologram is acquired at the plane, H. The two holograms are numerically combined and processed as described above to finally obtain the aberration-compensated image of the retina. Thus, the same holographic interferometer serves to achieve the sensing of the aberration field and compensation of the aberration. In comparison with conventional AO, a lenslet array 305, a second CCD camera 315, and a deformable mirror 300 are absent, significantly reducing the complexity and cost of the apparatus.

Figure 4:
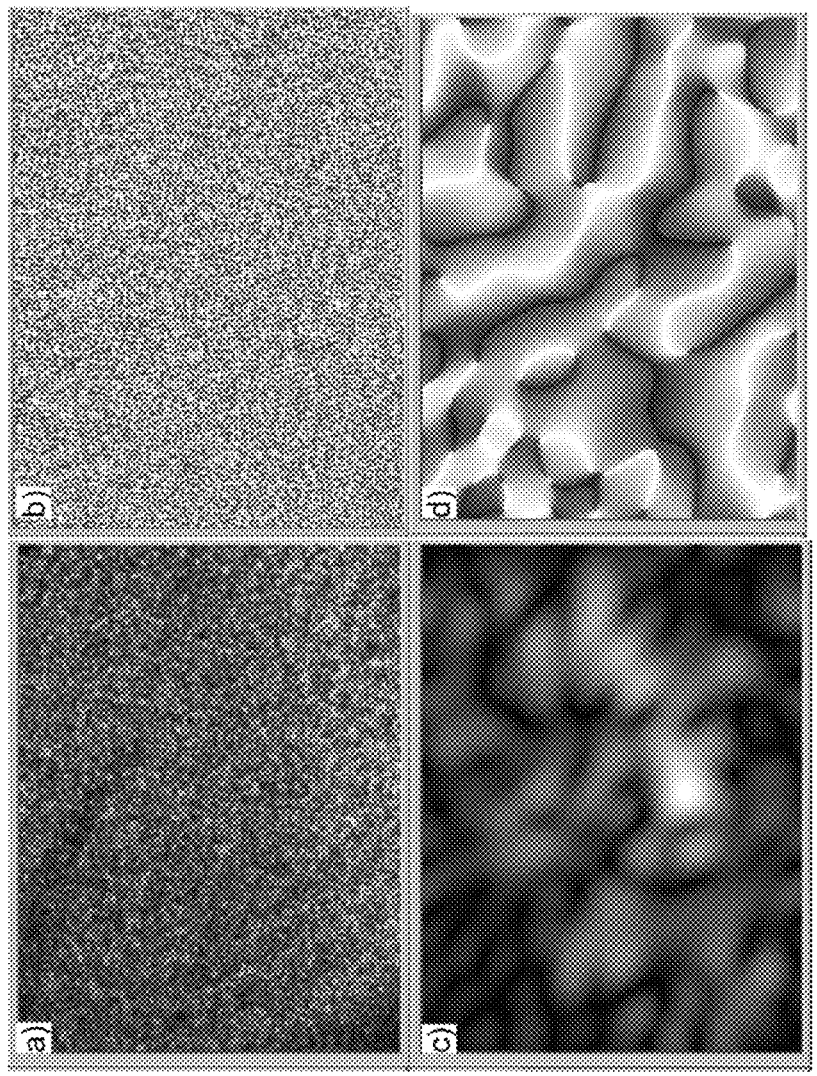
FIG. 4. is an illustration of (a) Amplitude and (b) phase of complex hologram with full-field illumination. (c) Amplitude and (d) phase of complex hologram with guide star illumination.

Hologram images are shown in FIG. 4. The field of view (FOV) on the retinal plane is 2134 μm×1601 μm with 1024 pixels×768 pixels. The amplitude and phase of the complex hologram with full-field illumination is shown in FIGS. 4(a) and 4(b). The complex hologram is obtained by taking the intensity hologram captured by the camera and numerically filtering one of the angular spectrum components [1-3]. The amplitude and phase of the complex hologram for guide star sensing is shown in FIGS. 4(c) and 4(d).

Figure 5:
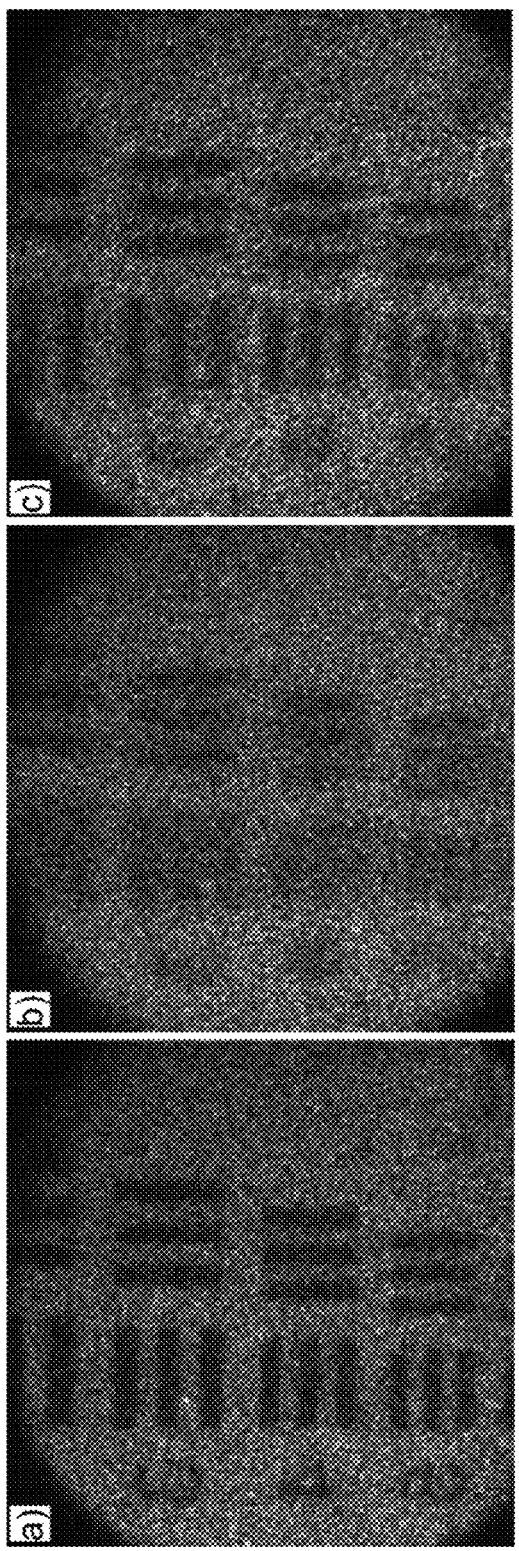
FIG. 5. Is a depiction of reconstructed images of the retinal plane (a) in the absence of an aberrator, (b) with an aberrator in place but without aberration correction, and (c) with an aberrator in place and after aberration correction.

The two holograms thus obtained are then used to reconstruct the retinal image. First, in FIG. 5(a), the image reconstructed from another hologram without the phase aberrator—the irregular piece of glass—in place is shown as a baseline. For reconstruction, we use a numerical lens of focal length 80 mm and the best image is obtained at a distance of 78 mm. The displayed image area corresponds to 1121 μm×1121 μm on the retinal plane and shows the elements 3-5 of group 3 of the USAF resolution target. Then, FIG. 5(b) is the image reconstructed from the complex hologram of FIGS. 4(a) and 4(b) without the aberration compensation, showing significant degradation of the resolution. Finally, in FIG. 5(c), the complex conjugate of the guide star hologram of FIGS. 4(c) and 4(d) is multiplied to the uncorrected hologram of FIGS. 4(a) and 4(b) before reconstruction. In both FIGS. 5(b) and 5(c), the best focus images are obtained at a distance of 76 mm, the difference with the case of FIG. 5(a) being likely due to the presence of the piece of glass with approximately 1:2 mm thickness. The RMS deviation of the wavefront is determined from FIG. 4(d) to be 1:11 μm, a rather severe value compared to those expected in the normal population. Compensation of the effect of the aberration and improvement of the resolution (better than ~40 μm) is quite evident, thus demonstrating the validity of the DHAO principle.

DHAO system have been demonstrated. The following are some of the features of the eye that can be imaged using the DHAO instrument.

Resolution of cone mosaic: Much of the benefit of adaptive optics stems from the ability to resolve individual photoreceptor cells, for example allowing identification of trichromatic cone mosaic. Resolution of cone mosaic will therefore be a benchmark of the effectiveness of the DHAO system.

Intraocular debris: From a single hologram, image can be formed at any distance within the object volume. Digital holography is highly effective in imaging and locating the positions of suspended particles with high precision, such as intraocular debris.

Vasculature: Disposition of blood vessels in the retina has obvious significance for the pathology of the eye. Imaging characteristics of blood vessels can be achieved by DHAO.

Blood flow: If the resolution is high enough, flow of blood cells in the vessels will represent rapidly changing areas against the rest of the field that is essentially static. Differential holography may be used to image the blood flow while suppressing the static background.

Dynamics of aberration: Time series of aberration profiles will be acquired that will reveal dynamic fluctuation of the aberration, which may be correlated with such factors as accommodation.

A self contained bench top DHAO instrument include the following systems:

Optical system: The general optical configuration is as described above. Polarization optics, apertures, and other filters may be added. Using a single laser source, optical chopper arrangement may be used for switching between the two illumination modes for sensing and imaging. Use of two separate lasers may be feasible. This will completely remove moving parts and improve timing flexibility, but may require unwrapping of phase before compensation and additional refinement of procedures. Means for varying the magnification of the imaging system will be provided from low magnification wide field imaging to high magnification microscopic imaging.

Mechanical system: Other than generic optomechanical setup of the apparatus, some specific considerations for the eye placement will be needed. A few different attachments may be implemented for the variety of imaging subjects, including eye models, excised animal eyes, or live animal eyes. Means to fine-adjust the position of the eye will be necessary.

Electronics system: Electronics should be mostly straightforward, including synchronization of illumination and the camera, and the interface with the computer.

Software system: Components of the software system includes timing; image acquisition; diffraction and holographic image calculation; wavefront profile generation; wavefront compensation; calibration; pre- and post-processing of images; image rendering; and image data handling and archiving. Particular attention is given to user-friendliness, programmability, and flexibility for modifying and implementing various functionalities. Overall speed of the imaging system will primarily depend on the core numerical algorithms. At least 10 Hz of frame rate is preferred. These algorithms can be implemented on field-programmable gate array (FPGA) and dedicated buffer memory. DHAO does not require computation of feedback. Therefore, depending on applications, camera images can be acquired in a continuous burst before proceeding with computations for image reconstruction and aberration compensation.

REFERENCES

1. E. Cuche, P. Marquet, and C. Depeursinge, Opt. Lett. 24, 291-293 (1999).

2. C. Mann, L. Yu, C. Lo, and M. K. Kim, Opt. Express. 13, 8693-8698 (2005).
3. M. K. Kim, SPIE Reviews 1, 1-50 (2010).

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A method of retinal imaging utilizing digital holography with adaptive optics capability but without a wavefront sensor or wavefront corrector, the method comprising:
   providing a narrow laser beam entering an eye through the cornea and lens, forming a focused spot on the retina, wherein the narrow laser beam is narrow enough such that an aberration in the cornea and/or the lens across the narrow laser beam is negligible;
   capturing, by digital holography, and numerically storing a narrow beam holographic wavefront profile of the emergent beam resulting from the narrow laser beam;
   providing a full-field illumination to the retina;
   capturing, by digital holography, and numerically storing a full-field illuminated holographic wavefront profile of the emergent light resulting from the full-field illumination; and
   numerically subtracting and processing the narrow beam holographic wavefront profile and the full-field illuminated holographic wavefront profile to obtain an aberration-compensated image of the retina.

2. The method of claim 1, wherein the narrow laser beam is a narrow collimated laser beam.

3. The method of claim 1, wherein capturing the narrow beam holographic wavefront profile and capturing the full-field illuminated holographic wavefront profile further comprises numerically filtering an angular spectrum component captured by a camera.

4. The method of claim 1, wherein the narrow beam holographic wavefront profile and the full-field illuminated holographic wavefront profile are profiles of the vasculature of a retina, said method being used to image blood flow.

5. The method of claim 1, wherein the narrow beam holographic wavefront profile and the full-field illuminated holographic wavefront profile are real-time profiles of ocular aberration, said method being used during refractive surgery and generating a three-dimensional map of intraocular debris.

6. The method of claim 1, wherein the aberration-compensated image comprises full 3-D content of the optical field, said method further comprising extracting an in-focus image of a larger area of the retina.

7. The method of claim 1, wherein the aberration-compensated image comprises 3-D content of the optical field, said method further comprising imaging particulate objects and determining their 3-D locations with high precision, producing a 3-D distribution map of the particulate objects.

8. The method of claim 1, wherein the narrow beam holographic wavefront profile is subtracted from the full-field illuminated holographic wavefront profile to remove the effect of aberration.

9. The method of claim 1, wherein the aberration-compensated image of a retina is represented by an array of complex numbers, including the amplitude and phase of the wavefront.

10. The method of claim 1, wherein a plurality of narrow beam holographic wavefront profiles and a plurality of full-field illuminated holographic wavefront profiles of the retina are acquired and used to obtain the aberration-compensated image of the retina.

11. A method of imaging a retina utilizing digital holography combined with conventional ophthalmic imaging, the method comprising:
   providing a narrow laser beam and a beam splitter;
   splitting the narrow laser beam into two parts at the beam splitter, a first part of the laser beam entering through the cornea and lens of an eye, forming a focused spot on the retina of the eye, wherein the first part of the laser beam is narrow enough such that an aberration in the cornea and/or the lens across the first part of the laser beam is negligible;
   capturing and numerically storing a narrow beam holographic wavefront profile of the emergent beam resulting from the narrow laser beam, relative to a reference beam provided by a second part of the laser beam;
   providing a full-field illumination to the retina of the eye;
   capturing and numerically storing a full-field illuminated holographic wavefront profile of the emergent beam resulting from the full-field illumination, relative to the reference beam provided by the second part of the laser beam; and
   numerically subtracting and processing the narrow beam holographic wavefront profile and the full-field illuminated holographic wavefront profile to obtain the aberration-compensated image of the retina.

12. The method of claim 11, wherein the narrow laser beam is a narrow collimated laser beam.

13. The method of claim 11, wherein capturing a narrow beam holographic wavefront profile and capturing a full-field illuminated holographic wavefront profile further comprises, numerically filtering an angular spectrum captured by a camera.

14. The method of claim 11, wherein the narrow beam holographic wavefront profile and the full-field illuminated holographic wavefront profile are profiles of the vasculature of a retina, said method being used to image blood flow.

15. The method of claim 11, wherein the narrow beam holographic wavefront profile and the full-field illuminated holographic wavefront profile are profiles are real time profiles of ocular aberration, said method being used during refractive surgery and generating three-dimensional map of intraocular debris.

16. The method of claim 11, wherein the aberration-compensated image comprises full 3-D content of the optical field, said method further comprising extracting an in-focus image of a larger area of the retina.

17. The method of claim 11, wherein the aberration-compensated image comprises full 3-D content of the optical field, said method further comprising imaging particulate objects and determining their 3D locations with high precision, producing a 3-D distribution map of such particles.

18. The method of claim 11, wherein the aberration-compensated image of the retina is represented by an array of complex numbers, including the amplitude and phase of the wavefront.

19. The method of claim 11, wherein a plurality of narrow beam holographic wavefront profiles and a plurality of full-field illuminated holographic wavefront profiles of the retina are acquired and used to obtain the aberration-compensated image of the retina.

20. An apparatus for imaging a retina utilizing digital holography without a wavefront sensor or a wavefront corrector, said apparatus comprising:
    an illumination system for providing a narrow laser beam and a full-field illumination of a retina of an eye, wherein the narrow laser beam passes through the cornea and the lens of the eye and wherein the narrow laser beam is narrow enough such that an aberration in the cornea and/or the lens across the narrow laser beam is negligible;
    an eye placement system;
    an optics system to capture a narrow laser beam digital holographic image of the retina and to capture a full-field illuminated digital holographic image of the retina and to reconstruct holographic data from the digital holographic images;
    a software system to process the holographic data by numerically subtracting the narrow beam holographic wavefront profile and the full-field illuminated holographic wavefront profile to obtain the aberration-compensated image of the retina obtained from the optics system; and
    an electronics system to synchronize the illumination system, the optics system and the eye placement system with the software system.

21. The apparatus of claim 20, wherein the software system stores the digital holographic obtained from the optics system.

22. The apparatus of claim 20, wherein the illumination system is an narrow collimated laser beam.

23. The apparatus of claim 20, wherein the software system performs timing, image acquisition, diffraction and holographic image calculation, wavefront profile generation, wavefront compensation, calibration, pre-processing and post-processing of images, image rendering, and image data handling and archiving.

* * * * *